United States Patent
Brehin et al.

(10) Patent No.: US 8,449,887 B2
(45) Date of Patent: May 28, 2013

(54) ANTI-CHIKUNGUNYA MONOCLONAL ANTIBODIES AND USES THEREOF

(75) Inventors: Anne-Claire Brehin, Paris (FR); Amadou Alpha Sall, Dakar (SN); Philippe Despres, La Garenne Colombes (FR)

(73) Assignee: Institut Pasteur, Paris (FR)

( * ) Notice: Subject to any disclaimer, the term of this patent is extended or adjusted under 35 U.S.C. 154(b) by 96 days.

(21) Appl. No.: 12/676,780

(22) PCT Filed: Sep. 4, 2008

(86) PCT No.: PCT/IB2008/003092
§ 371 (c)(1),
(2), (4) Date: Feb. 24, 2011

(87) PCT Pub. No.: WO2009/031045
PCT Pub. Date: Mar. 12, 2009

(65) Prior Publication Data
US 2011/0143333 A1  Jun. 16, 2011

(30) Foreign Application Priority Data
Sep. 7, 2007 (CA) ..................................... 2598966

(51) Int. Cl.
*A61K 39/395* (2006.01)
*C12Q 1/70* (2006.01)

(52) U.S. Cl.
USPC ........................................ 424/147.1; 435/7.1

(58) Field of Classification Search
None
See application file for complete search history.

(56) References Cited

U.S. PATENT DOCUMENTS

2010/0055105 A1 * 3/2010 Despres et al. ............ 424/139.1

OTHER PUBLICATIONS

Blackburn et al. Res. Virol. 1995, vol. 146, (1), pp. 69-73.*

* cited by examiner

*Primary Examiner* — Bao Li
(74) *Attorney, Agent, or Firm* — Finnegan, Henderson, Farabow, Garrett & Dunner, L.L.P.

(57) ABSTRACT

The present invention relates to the field of arbovirosis caused by Chikungunya virus (CHIK). The present invention specifically concerns anti-CHIK monoclonal antibodies (MAbs), and more specifically anti-CHIK.E2 MAbs and their use as diagnostic products in methods for detecting the presence or absence of a CHIK strain.

11 Claims, 8 Drawing Sheets

```
[1-50]     STKDNFNVYKATRPYLAHCPDCGEGHSCHSPVALERIRNEATDGTLKIQV    CHIK.06-49 SEQ ID NO: 1
           NARE------V--------------------I------S-----------    Igbo-Ora IBH10964 SEQ ID NO: 2
           NARE------V--------------------I------S-----------    ONN-59 SEQ ID NO: 3

[51-100]   SLQIGIKTDDSHDWTKLRYMDNHMPADAERAGL FVRTSAPCTITGTMGHF   CHIK.06-49
           --------A------------S-T-V--D-S-------------------    Igbo-Ora IBH10964
           ---------------------S-T-V--D-S-------------------    ONN-59

[101-150]  ILARCPKGETLTVGFTDSRKISHSCTHPFHHDPPVIGREKFHSRPQHGKE    CHIK.06-49
           ---------------V---R---T-M-----E--L---------------    Igbo-Ora IBH10964
           ---------------V---R---T-M---R-E--L---------------    ONN-59

[151-200]  LPCSTYVQSTAATTEEIEVHMPPDTPDRTLMSQQSGNVKITVNGQTVRYK    CHIK.06-49
           -------HT-------------------Y-L-T--A-------D------    Igbo-Ora IBH10964
           -------HT----A--------------Y-L-T--A-------D------    ONN-59

[201-250]  CNCGGSNEGLTTTDKVINNCKVDQCHAAVTNHKKWQYNSPLVPRNAELGD    CHIK.06-49
           -K-D--------------------T-----------------T---S-Q-    Igbo-Ora IBH10964
           -K-D--------------------T-----------------T---S-Q-    ONN-59

[251-300]  RKGKIHIPFPLANVTCRVPKARNPTVTYGKNQVIMLLYPDHPTLLSYRNM    CHIK.06-49
           -----------V-T------------------R-TL------------A-    Igbo-Ora IBH10964
           -----------V-T------------------R-TL--H---------A-    ONN-59

[301-350]  GEEPNYQEEWVMHKKEVVLTVPTEGLEVTWGNNEP YKYWPQLSTNGTAHG   CHIK.06-49
           -RI-D-H---ITS---ISI---A----------D----------------    Igbo-Ora IBH10964
           -RI-D-H---ITN---ISI---A----------D----------------    ONN-59

[351-364]  HPHEIILYYYELYP                                        CHIK.06-49
           --------------                                        Igbo-Ora IBH10964
           --------------                                        ONN-59
```

US 8,449,887 B2

ANTI-CHIKUNGUNYA MONOCLONAL ANTIBODIES AND USES THEREOF

SEQUENCE LISTING

The instant application contains a Sequence Listing which has been submitted in ASCII format via EFS-Web and is hereby incorporated by reference in its entirety. Said ASCII copy, created on Feb. 8, 2011, is named 88002001.txt and is 10,524 bytes in size.

FIELD OF THE INVENTION

The present invention relates to the field of arbovirosis caused by Chikungunya virus (CHIK). The present invention specifically concerns anti-CHIK monoclonal antibodies (MAbs), and more specifically anti-CHIK.E2 MAbs and their use as diagnostic products in methods for detecting the presence or absence of a CHIK strain.

BACKGROUND OF THE INVENTION

Chikungunya (CHIK) virus has the ability to cause explosive epidemics in Africa, India, and southeast Asia (Epstein, 2007; reviewed by Powers and Logue, 2007). The virus is transmitted by mosquitoes of genus *Aedes* (Ae.). CHIK virus has been responsible for unprecedented magnitude outbreaks in Reunion Island and Indian Ocean since 2005, and in India where an estimated 1.4 million inhabitants have been infected in 2006 (Schuffenecker et al., 2006; Staikowsky et al., 2006; Arankalle et al., 2007; reviewed by Pialoux et al., 2007).

Humans infected with CHIK virus typically experience acute illness with incapacitating polyarthralgia, severe muscle pain and stiffness in the joints sometimes followed by a maculopapular rash (Johnston and Peters, 1996; Borgherini et al., 2007; reviewed by Pialoux et al., 2007; Rulli et al., 2007). CHIK virus infection is associated in almost all cases with myalgias. CHIK virus infection of satellite cells within the muscles could explain, in part, some features of clinical manifestations (Ozden et al., 2007). The clinical symptomes of Chikungunya virus infection are often misdiagnosed for arboviral diseases due to other arthritogenic alphaviruses such as Igbo-Ora virus from Western Africa, O'nyong-nyong (ONN) virus from Central Africa, Ross River and Barma viruses from Australia and the Pacific, Mayaro virus from South America, and cosmopolitan Sindbis (SIN) virus.

CHIK virus is a member of the genus *Alphavirus* and family Togaviridae (reviewed by Strauss and Strauss, 1994). The alphaviruses are small enveloped single—stranded positive RNA viruses exhibiting a large cell tropism. The viral surfaces are covered in membrane-anchored spikes composed of triplets of heterodimers of the envelope E1 and E2 glycoproteins. The viral spike proteins facilitate attachment to cell surfaces and viral entry. The E1 envelope glycoprotein is a class II fusion protein that mediates low pH-triggered membrane fusion during virus infection. E2 is a 50 kDa type I transmembrane glycoprotein: the first 260 amino acids constitute the ectodomain, followed by about 100 amino acids that form the stem region, a spanning region of 30 amino acids, and a short cytoplasmic endodomain of 30 amino acids (Pletnev et al., 2001; Mukhopadhyay et al., 2006). pE2 (the 62-kDa precursor to the E3 and E2 proteins) and E1 are assembled as heterodimers in the endoplasmic reticulum (reviewed by Strauss and Strauss, 1994). After the cleavage of pE2 in the Golgi apparatus to form E3 and E2, the E1-E2 complexes are transported to the plasma membrane (PM). The interaction of the cytoplasmic E2 endodomain with the preassembled nucleocaspid is one of the initial steps in the process of virus envelopment at the PM. Integrity of virion is maintained by direct interactions between E1 and E2 (Strauss and Strauss, 1994). During the course of alphavirus life cycle, the E2 glycoprotein is responsible for receptor binding. Most neutralizing antibodies recognize epitopes in E2 rather than E1 (reviewed by Strauss and Strauss, 1994). Antibodies that recognize conformational epitopes on the outer surface of E2 have the potential to neutralize alphavirus infection.

Biological diagnosis of CHIK virus infection is essentially based on quantitative real-time RT-PCR-based method during the initial viraemic phase (Edwards et al., 2007; Laurent et al., 2007; Santhosh et al., 2007). Serological methods detect anti-CHIK IgM early times after the first clinical manifestations and specific IgG after two weeks (reviewed by Pialoux et al., 2007). However, ELISA and immunodetection assays are poorly specific and sensitive due the cross reactivity of CHIK virus with related members of the Semliki Forest (SF) antigenic complex (Greiser-Wilke et al., 1991).

BRIEF DESCRIPTION OF THE FIGURES

FIG. 7: Alignment of E2 sequences of CHIK (SEQ ID NO: 1), Igbo-Ora (SEQ ID NO: 2) and ONN viruses (SEQ ID NO: 3), showing the region from residues E2-1 to E2-364. The asparagine-linked glycosylation sites are marked with (♦). The open frames indicate the three specific amino acid differences in ONN virus as compared to CHIK and Igbo-Ora viruses.

BRIEF DESCRIPTION OF THE INVENTION

Figure 1:
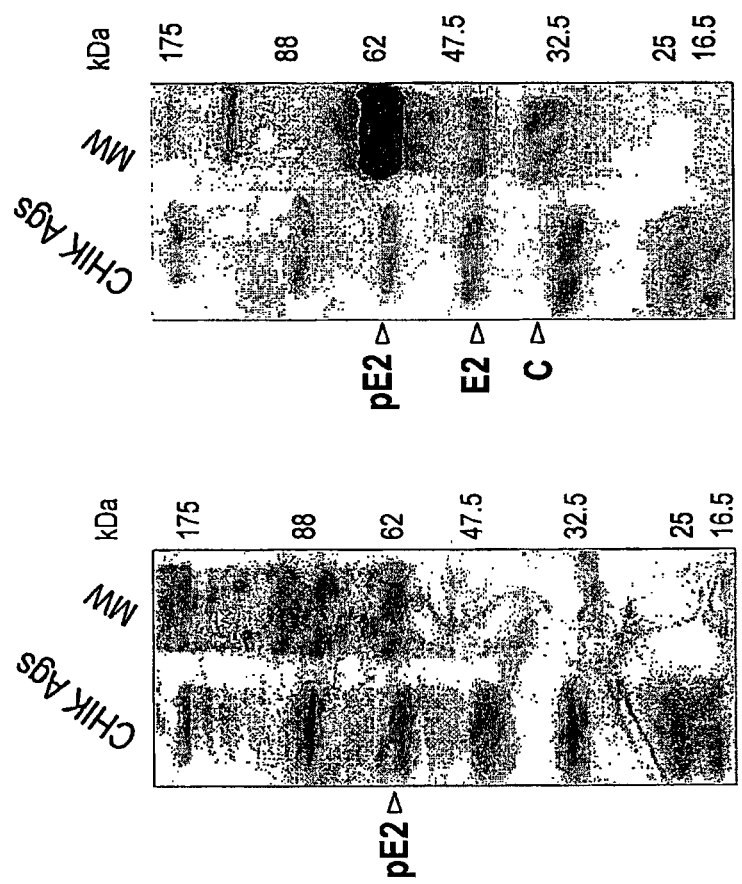
FIG. 1: CHIK protein composition and antigenic specificity of viral preparation. CHIK antigens (CHIK Ags) were separated by 4-12% SDS-PAGE under denaturing conditions and directly visualized by Coomassie blue staining (left) or electroblotted onto a PVDF membrane for immunoblot analysis using anti-CHIK HMAF (right). The positions of molecular weight markers (MW) are indicated in kDa.

The inventors have developed and characterized monoclonal antibodies (MAbs) that find a particular advantage in the studying of the biology of CHIK virus and pathogenesis of CHIK related disease.

As one in the art may appreciate, the originality of the present invention resides in the fact the inventors have produced and characterized a panel of monoclonal antibodies (MAbs) which specifically bind to the whole CHIK virus or to the CHIK E2 glycoprotein, even to its soluble form.

In this connection, the present invention provides a monoclonal antibody that specifically binds to an epitope located on the outer surface of a CHIK virus, such as those deposited at the CNCM (Collection Nationale de Cultures de Microorganismes), 28 rue du Docteur Roux, 75724 Paris Cedex 15, on Sep. 6, 2007 under accession number I-3822 (3C3), I-3824 (3E4), and I-3823 (8A4). As used herein, the term "specifically binds to" refers to antibodies that bind with a relatively high affinity to a CHIK protein contemplated by the present invention, such as the E2 glycoprotein, but which do not substantially recognize and bind to molecules other than the CHIK E2 glycoprotein. As used herein, the term "relatively high affinity" means a binding affinity between the antibody and the protein of interest of at least $10^{-6}$ M, and preferably of at least about $10^{-7}$ M and even more preferably $10^{-8}$ M to $10^{-10}$ M. Determination of such affinity is preferably conducted under standard competitive binding immunoassay conditions which is common knowledge to one skilled in the art.

As used herein, the term "antibody" refers to a glycoprotein produced by lymphoid cells in response to a stimulation with an immunogen. Antibodies possess the ability to react in vitro and in vivo specifically and selectively with an antigenic determinant or epitope eliciting their production or with an antigenic determinant closely related to the homologous antigen. The term "antibody" is meant to encompass constructions using the binding (variable) region of such an antibody, and other antibody modifications. Thus, an antibody useful in the method of the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

The monoclonal antibodies of the present invention or combination thereof, find a particular use as diagnosis reagents, and/or for the screening of a CHIK infection even if such infection is asymptomatic. The monoclonal antibodies of the invention find a further use in diagnostic methods which may include but not limited to, immunofluorescence, immunoblot and ELISA assays.

In this connection, the present invention provides a method for detecting the presence or absence of a Chikungunya virus (CHIK) strain in a sample, comprising the steps of:
  a) contacting the sample with an anti-CHIK monoclonal antibody of the present invention or with a combination of anti-CHIK monoclonal antibodies of the invention to form an immune complex; and
  b) detecting the presence or absence of the immune complex formed in a).

More specifically, the present invention concerns a method for detecting the presence or absence of envelope E2 polypeptide or functional derivative or its precursor E3E2 (p62) from Chikungunya (CHIK) E2 polypeptide in a sample, comprising the steps of:
  a) contacting the sample with an anti-CHIK E2 monoclonal antibody of the present invention or with a combination of anti-CHIK monoclonal antibodies of the invention to form an immune complex; and
  b) detecting the presence or absence of the immune complex formed in a).

As used herein, the term "functional derivative" refers to a fragment of the E2 glycoprotein, such as the E2 ectodomain, that still retain the capacity of being recognized by the monoclonal antibodies of the present invention. The term "epitope" refers to the site on an antigen, such as the E2 glycoprotein, to which a specific antibody molecule, such as the monoclonal antibodies of the invention, binds. As used herein, the term "sample" refers to a variety of sample types obtained from an individual and can be used in a diagnostic or detection assay in accordance with the present invention. The definition encompasses blood and other liquid samples of biological origin, solid tissue samples such as a biopsy specimen or tissue cultures or cells derived therefrom, and the progeny thereof.

As one may appreciate, in the case where a combination of anti-CHIK monoclonal antibodies is used, one monoclonal antibody may consists on a capture antibody, such as 8A4, and a second monoclonal antibody may consists of a detecting antibody, such as 3E4. Such a capture and a detecting antibodies may find, for instance, an advantageous use in a ELISA assay.

The present invention also concerns kit for detecting the presence or absence of a Chikungunya virus (CHIK) strain in a sample, and more specifically for detecting the presence or absence of a Chikungunya virus (CHIK) E2 polypeptide in a sample. The kits comprise at least one monoclonal antibody selected from the group deposited at the CNCM (Collection Nationale de Cultures de Microorganismes), 28 rue du Docteur Roux, 75724 Paris Cedex 15, on Sep. 6, 2007 under accession number I-3822 (3C3), I-3824 (3E4), and I-3823 (8A4). Kits according to this embodiment of the invention may comprise packages, each containing one or more of the above mentioned monoclonal antibodies (typically in concentrated form) which are required to perform the respective diagnostic tests.

EXAMPLE

Production and Characterization of Mouse Monoclonal Antibodies Reactive to Chikungunya Envelope E2 Glycoprotein Chikungunya fever is an arbovirosis of major impact in public health in Asia and Africa. Chikungunya (CHIK) virus is member of the genus *Alphavirus* and belongs to the Semliki Forest (SF) antigenic complex. The inventors describe for the first time a panel of monoclonal antibodies (MAbs) reactive to CHIK envelope E2 glycoprotein. For the screening of E2-specific MAbs, the inventors expressed a recombinant soluble CHIK E2 protein in *Drosophila* S2 cells. Analyzed by immunological methods, MAbs 3C3, 3E4, and 8A4 were selected on the basis of their reactivity. Their epitopes are located to the outer surface of CHIK virions. These MAbs have no cross reactivity with related members of SF antigenic complex with the notable exception of Igbo-Ora virus. Anti-CHIK E2 MAbs 3C3, 3E4, and 8A4 are helpful for studying the biology of CHIK virus and pathogenesis of disease. The combination of 8A4 and 3E4 is suitable for developing a specific antigen-capture ELISA.

Materials and Methods
Cell Lines and CHIK Viruses

Vero cells were grown in Dulbecco's modified Eagle's growth medium (DMEM) (Invitrogen) supplemented with 5% heat inactivated foetal bovine serum (FBS) and 2 mM L-Glutamine. The 293A cells (Quantum) were grown in DMEM growth medium with pyruvate (Invitrogen) supplemented with 10% FBS and 2 mM L-Glutamine. Vero and 293A cells were incubated at 37° C. under $CO_2$. The *Aedes pseudoscutellaris* AP61 mosquito cells were grown in Leibovitz L-15 growth media supplemented with 10% FBS and 1% tryptose-phosphate broth (Eurobio). The *Drosophila melanogaster* Schneider 2 (S2) cell line was purchased from Invitrogen. S2 cells were grown in Schneider's growth medium (Invitrogen) with 10% FBS. Invertebrate AP61 and S2 cells were incubated at 27° C. All media were supplemented with penicillin and streptomycin antibiotics.

CHIK.06-49 virus (genotype 4) was isolated from a young adult during the 2006 outbreak of Chikunungya fever in La Réunion island (Schuffenecker et al., 2006). The virus was twice passaged on mosquito cell lines. Virus stocks were titered by standardized AP61 cell focus immuno assay (FIA) using anti-CHIK HMAF and titers were expressed as $FFU \cdot mL^{-1}$ (Schuffenecker et al., 2006). High concentrations of purified CHIK.06-49 were obtained from infected mosquito cells. Briefly, twenty flasks of AP61 cell monolayers were inoculated with CHIK virus at a multiplicity of infection (MOI) of 0.4 FFU per cell. The supernatant fluids of infected cells were harvested two days postinfection and clarified. Virus was precipitated with 10% (wt:vol) polyethylene glycol (PEG) 8,000 (Fluka) in 0.5 M NaCl at 4° C. for 4 h. After centrifugation, the pellet was resuspended in TNE buffer (20 mM Tris-Cl [pH 8.0], 150 mM NaCl, 2 mM EDTA) and centrifuged on a discontinuous sucrose gradient composed of 60% (wt:wt) and 30% (wt:vol) of sucrose at 39,000 rpm at 4° C. for 2 h. The visible band at the interface was harvested and diluted in TNE buffer. The virus was further purified on a continuous 11-52% (w/v) sucrose gradient at 35,000 rpm at 4° C. for 18 h. The visible band was harvested, aliquoted, and stored at −80° C.

Production of CHIK Antigens

High concentrations of CHIK antigens were generated from virus particles. Forty flasks of AP61 cell monolayers were inoculated with CHIK.06-49 virus at 0.4 MOI. The supernatant fluids of infected cells were harvested two days postinfection and clarified. Virus particles were precipitated with PEG 8,000 in the presence of 0.5 M NaCl as described above. The pellet resuspended in TNE buffer was supplemented with 20 mM triethanolamine (Sigma) and then incubated with 2% Triton X-100 (Sigma) for 10 min on ice. The suspension was centrifuged for 1 min at 2,000 rpm and the clarified preparation was applied to a 10 to 30% continuous sucrose gradient and centrifuged at 35,000 rpm for 16 h at 4° C. Fractions were collected from the top and assessed by Coomassie blue staining on SDS-PAGE and Immunoblotting. Pooled fractions containing CHIK antigens (viral preparation) were UV inactivated and the residual infectivity was verified by FIA.

Production of Antibody-Producing Hybridoma Clones

Three µg of viral preparation were emulsified in equal ratio with Freund's complete adjuvant (Sigma). Four 11-week-old BALB/c mice (Charles River) were immunized by subcutaneous injections. Two booster injections were administered at the same doses at three-week intervals. Mice were bled ten days after each boost. A pre-fusion boost was administered four days before fusion (same dose divided in four injections, two subcutaneous injections and then two intraperitoneal injections).

Sp2/0Ag14 myeloma cell line was fused with splenocytes from immunized mice according to standard protocols. Antibody-producing hybridomas were twice sub-clones and then frozen in liquid nitrogen. Monoclonal antibodies were produced in vitro by collecting high concentrated supernatants. Purifications were done by affinity chromatography on n-protein A Sepharose (GE Healthcare). The MAbs were isotyped with a mouse mAb isotyping test kit (AbD Serotec) according to the manufacturer's recommandations.

Construction and Expression of Recombinant Soluble CHIK sE2 Protein

The CHIK.06-49 sequence (Genbank accession n° AM258994) coding for the ectodomain followed by the stem region of E2 (residues E2-4 to E2-364) was amplified from TOPO plasmid containing the CHIK.06-49 pE2 gene using PCR with forward primer 5'-AAAAAAGATCTGACAACTTCAATGTCTATAAAGCCACAAGACC-3' (SEQ ID NO: 4) and reverse primer 5'-TTTTTGCGGCCGCGTCATAGTGGGGTACAG CTCATAATAATACAG-3' (SEQ ID NO: 5). The PCR product was digested with Bgl II and Not I and then inserted into the unique Bgl II and Not I sites of the pMT/Bip/V5-HisA plasmid (Invitrogen) to generate pMT/BiP/CHIK.sE2. The CHIK sE2 sequence was placed in-frame with a BiP sequence which directs recombinant protein to the secretory pathway. In the expression vector, the CHIK sE2 sequence is followed at its C-terminus by the V5 epitope and six histidines (SEQ ID NO: 6) for affinity purification using nickel chelate affinity chromatography. *Drosophila* S2 cells (Invitrogen) were transfected by the recombinant plasmid pMT/BiP/CHIK.sE2 using the Calcium Phosphate Transfection Kit (Invitrogen). Stably transfected cells were selected by adding 25 µg/ml blasticidin over several weeks. Cultured S2 cells expressing CHIK.sE2 protein were adapted in serum-free growth medium containing 10 µg/ml blasticidin. $CuSO_4$ was added to final concentration of 500 µM to induce synthesis and secretion of recombinant soluble CHIK.E2 protein. Accumulation of CHIK.sE2 in the culture medium was maximal 10 days after addition of CuSO4. The cell culture supernatants were passed on 0.2 µM filters. Protein samples were concentrated through 10,000-MWCo Vivaspin columns (Vivasciences) and then dialyzed in PBS. Alternatively, recombinant CHIK.sE2 protein was purified from cell culture supernatant on equilibrated chelating column chromatography (HiTrap Chelating HP, Amersham). The column was washed several times with washing buffer (0.5 M NaCl, 50 mM sodium phosphate buffer, [pH 8.0]) and bound CHIK.sE2 was eluted with increasing concentration of imidazole. Fractions containing CHIK.sE2 proteins were pooled and dialyzed in PBS. Soluble form of DEN-1, E glycoprotein (DEN-1 sE) was also produced in *Drosophila* S2 cells.

Kinetic Ranking Assays

The kinetic ranking assays were performed on a ProteOn XPR 36 instrument (Bio-Rad) and data analysis was performed using ProteOn Manager software (Bio-Rad). Anti-mouse IgG (Sigma), was immobilized on a GLM sensorchip (Bio-Rad) using a standard amine coupling chemistry. The running buffer TPBS (0.005% Tween-20 in PBS) was used continuously throughout the entire experiment at 25° C. Briefly, 0.2 mL of a mixture of 0.2 M EDC and 0.05 M Sulfo-NHS was injected at a flow rate of 0.030 mL·min$^{-1}$, followed by 0.2 mL of 0.075 mg·mL$^{-1}$ anti-mouse IgG diluted in 10 mM Na-acetate buffer at pH 4.5. The surface was then deactivated with 0.15 mL of 1 M ethanolamine pH 8.5. Hybridoma supernatants diluted 1:2 in TPBS supplemented with 1 mg·mL$^{-1}$ alginate was injected under 0.2 mL at a flow rate of 0.025 mL·min$^{-1}$, followed by 0.2 mL of increasing concentrations of recombinant soluble CHIK.sE2 protein.

Indirect ELISA

For indirect ELISA, a Maxisorp plate (Nalgen Nunc), was coated with $10^5$ FFU of sucrose-purified CHIK virions diluted in D-PBS (Invitrogen), 50 of CHIK antigens used for immunizations or 50 ng of recombinant soluble CHIK.sE2 protein and incubated overnight at 4° C. Non-specific protein binding sites were blocked with 3% milk in PBS for 1 h at 37° C. Plates were washed with PBS containing 0.1% Tween-20 (PBST). Sera from immunized mice, serially diluted in PBST, milk 0.1%, and cell culture supernatants 1:2, diluted in the same buffer, were added and incubated at 37° C. for 2 hours in the coated plates. After washing with PBST, a 1:5,000 dilution peroxidase-conjugated AffiniPure Goat anti-Mouse IgG (H+L) (Jackson ImmunoResearch) containing 1% milk was added for 1 h at 37° C. After washing, 3,3',5,5'-tetramethylbenzidine base substrate (TMB, KPL) was added. The color reaction was stopped with 0.1 mL of 1M $H_3PO_4$, to each well and the plates were examined at 450 nm in an OpsysMR ELISA reader (Dinex Technologies).

Antigen-Capture ELISA

To prepare detecting MAb, the purified MAb were labeled with peroxide oxidoreductase (POD) to the amine group of antibody as previously described (Nakane and Kawaoi, 1974). The purified MAb for the antigen-capture was immobilized on Maxisorp plates (Nalgen Nunc) by incubating 2 µg·mL$^{-1}$ antibody in 0.1 mL carbonate buffer [pH 9.2] overnight at room temperature. The wells were then washed twice with TPBS, followed by blocking with 8% (wt/vol.) sucrose in PBS supplemented with 3% skimmed milk for 1 h at 37° C. After removing the blocking agent, plates were dessicated for 10 min at 50° C., the wells dried and stored at 4° C. prior to use. Virus culture supernatant or recombinant soluble CHIK.sE2 protein diluted in PBST with 1% skimmed milk was added to the wells (0.1 mL/well) and incubated for 1 h at 37° C. After several washes, the wells were incubated for 1 h at 37° C. with 1 µg·mL$^{-1}$ per well of POD-conjugated MAb (0.1 mL/well) in PBST with 1% skimmed milk. After washing, TMB substrate was added and the plates were further incubated in darkness for 8 min. Enzymatic activity was measured as described above.

Immunoblot Analysis

Protein samples mixed with Laemmli sample buffer at room temperature were loaded on the 4-12% SDS-PAGE (NuPage, Invitrogen). Samples were electrotransferred onto a PVDF membrane (invitrogen) and blocked with 5% milk in PBST. Membrane was probed with primary antibody and the bound antibodies were detected by POD-conjugated secondary antibody at dilution 1:10,000 followed by ECL substrate solutions (Amersham).

IF Assay and Flow Cytometry Analysis

For indirect immunofluorescent (IF) assay, cells grown on Permanox Labtek chambers (Nunc) were fixed with 3.2% paraformaldehyde (PFA) in PBS for 20 min and then incubated with 50 mM $NH_4Cl$ in PBS for 10 min. Cells were permeabilized or not with 0.1% Triton X-100 in PBS for 4 min and then incubated with primary antibody in PBS/0.2% gelatin at 37° C. for 30 min. After extensive washing with PBS, cells were further incubated with fluorescein-conjugated goat anti-mouse IgG (Pierce) at 1:100 dilution in PBS/0.2% gelatin at 37° C. for 30 min. The samples were observed by fluorescence microscopy.

For flow cytometry flux, cells were unstuck and then fixed with 3.2% PFA in PBS. Fixed cells were extensively washed with staining buffer SB (0.1% [w/v] sodium azide in 1% FBS; pH 7.5), and incubated with primary antibody diluted in SB or in permeabilization buffer PB (SB buffer supplemented with 1% [wt./vol.] saponin) at 37° C. for 90 min. After extensive washing, cells were incubated with the fluorescein-conjugated secondary antibody (Pierce) 1:100 diluted in SB or PB at 37° C. for 1 h. After extensive washing, cells were analyzed by flow cytometry using a FACSCalibur (Becton Dickinson) with CellQuest Pro software (BD Biosciences).

Results

Production of CHIK E2 Antigens

Figure 2:
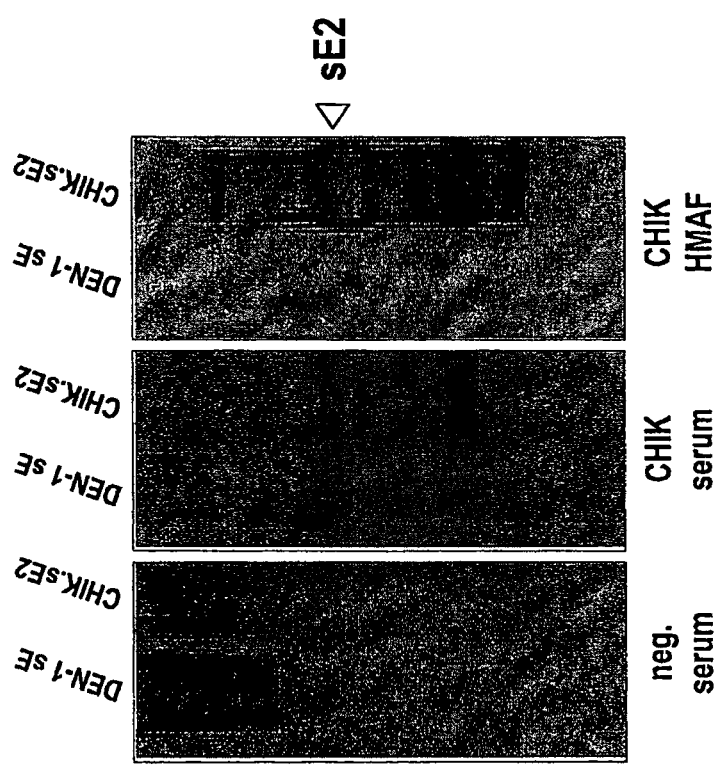
FIG. 2: Antigenicity of recombinant soluble CHIK sE2 glycoprotein. Immunoblot analysis was performed with purified recombinant soluble CHIK.sE2 protein and DEN-1 sE, anti-CHIK HMAF (CHIK HMAF), normal human serum (neg. serum), and CHIK positive patient serum (CHIK pos. serum)

In order to produce viral antigens, CHIK virions were precipitated from supernatants of mosquito cells infected by La Réunion island strain 06-49 of CHIK virus (CHIK.06-49). High concentrations of virus particles were incubated with 2% Triton X-100 and viral suspensions were applied to a sucrose gradient. After centrifugation, fractions were assessed by Immunoblot analysis. Anti-CHIK antibodies detected pE2, C and a much lesser extent E2 at about 15-20% sucrose concentration. The fractions enriched in pE2, E2 and C were pooled and treated with U.V. in order to perform the immunization of mice in a BSL-2 laboratory. As assessed by Coomassie blue staining of SDS-PAGE and Immunoblotting (FIG. 1), the major band observed after separation of viral antigens corresponded to pE2. The antigenicity of viral preparation was confirmed by indirect ELISA using anti-CHIK hyperimmune mouse ascitic fluids (HMAF) (data not shown). As negative controls, mouse immune sera directed against dengue (DEN) or West Nile virus showed no reactivity.

Because arbovirus antigens produced in *Drosophila* S2 cells could resemble their mosquito native counterparts, we expressed CHIK E2 glycoprotein using the *Drosophila* Expression System (Invitrogen). A stably transfected S2 cell line expressing the ectodomain followed by the stem of E2 from CHIK.06-49 virus (designated hereafter CHIK.sE2) has been established. Addition of CuSO4 to the culture medium induced the synthesis and secretion of recombinant soluble CHIK.sE2 protein. Accumulation of CHIK.sE2 in the culture medium was maximal two weeks after induction. For indirect ELISA, secreted CHIK.sE2 proteins were directly concentrated from supernatants and used to coat the ELISA plates. For Immunoblot analysis and antigen-capture ELISA, recombinant soluble CHIK.sE2 protein was purified from cell culture medium using nickel chelate affinity chromatography.

Immunoblot analysis demonstrated that recombinant soluble CHIK.sE2 protein (apparent molecular mass of 42 kDa) was recognized by anti-CHIK HMAF and CHIK positive patient serum (FIG. 2). Similar results were observed using indirect ELISA (data not shown). These results suggest that recombinant soluble CHIK.sE2 protein secreted from S2 cells has a conformation that is closer to the native form of the CHIK E2 glycoprotein.

Production of MAbs Directed Against CHIK E2 Protein

Figure 3:
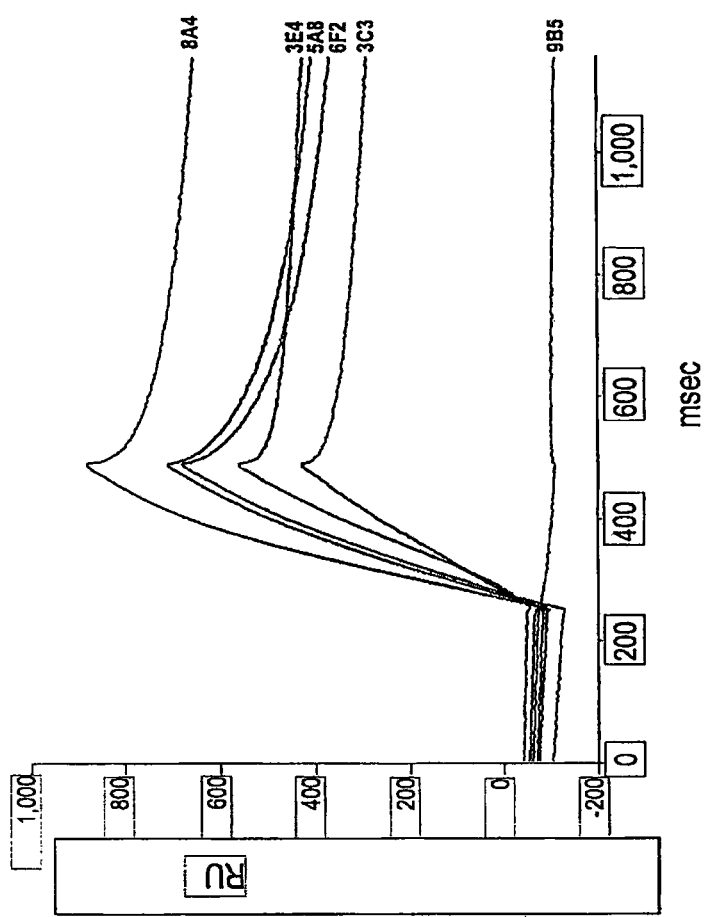
FIG. 3: Kinetic ranking assays on antibody-producing hybridoma supernatants. The curves show the monitored binding in resonance unit (RU) of 50 mM CHIK.sE2 protein on antibody-producing hybridoma supernatants 3C3, 3E4, 5A8, 6F2, 8A4, and 9B5 over time.

Two successful fusions were achieved using spleen cells from BALB/c mice immunized with viral preparation as described in Materials and Methods sections. For screening of antibody-producing hybridoma clones, viral preparation and recombinant soluble CHIK.sE2 protein were used as CHIK antigens in indirect ELISA. Approximately sixty antibody-producing hybridoma clones were identified as having antibody binding that were at least four-fold higher than the background level reactivity of foetal bovine serum (FBS). Twelve out of sixty hybridoma clones were able to react with sucrose-purified CHIK virions as well as recombinant soluble CHIK.sE2 protein by indirect ELISA (data not shown). Screened by IF assay, five antibody-producing hybridoma clones (3C3, 3E4, 5A8, 6F2, and 8A4) showed strong positive reaction against CHIK virus-infected cells (data not shown). ProteOn biosensor analysis showed that the five clones recognized CHIK.sE2 with high apparent binding affinity (FIG. 3). Three out of five antibody-producing hybridoma clones (3C3, 3E4, and 8A4) showed rapid association and slow dissociation of recombinant soluble CHIK.sE2 protein (data not shown). According to these results, antibody-producing hybridoma clones 3C3, 3E4, and 8A4 have been subcloned and then expanded. The following experiments were performed using purified anti-CHIK.E2 MAbs from hybridoma clone supernatants.

The characteristics of MAbs 3C3, 3E4, and 8A4 are summarized in Table 1.

TABLE 1

Characteristics of anti-CHIK.E2 MAbs

| MAb | Isotype | IF assay | Indirect ELISA | | Immunoblotting | |
| --- | --- | --- | --- | --- | --- | --- |
| | | | CHIK virus | CHIK.sE2 | CHIK virus | CHIK.sE2 |
| 3C3 | IgG1, κ | + | + | + | + | + |
| 3E4 | IgG1, κ | + | + | + | + | + |
| 8A4 | IgG1, κ | + | + | + | − | + |

The three anti-CHIK.E2 MAbs were of the subclass IgG1, κ. Focus reduction neutralization tests (FRNT) were used to evaluate the ability of purified anti-CHIK.E2 MAbs to inhibit CHIK virus replication in cultured Vero cells. The end-point titer was calculated as the highest antibody dilution tested that reduced ~100 Focus Forming Units on AP61 cells (FFU) of CHIK.06-49 virus by at least 90% (FRNT90). While the anti-CHIK HMAF gave a FRNT90 of means of dilution 1:2,500, neither MAb 3C3, MAb 3E4, nor MAb 8A4 neutralized CHIK virus at concentration as high as $10 \, \mu g \cdot mL^{-1}$ (data not shown).

Reactivity of anti-CHIK.E2 MAbs with Native-Form of CHIK E2 Glycoprotein

Indirect ELISA tests were performed on CHIK virus to assess whether the selected anti-CHIK.E2 MAbs recognize the surface of the virion. In this goal, sucrose-purified CHIK.06-49 virus was used to coat the ELISA plates at $10^5$FFU per well and increasing concentrations of MAbs were added. MAbs 3C3, 3E4, and 8A4 reacted with native virus particles in indirect ELISA (FIG. 4), suggesting that their epitopes are exposed on the outer surface of CHIK virus.

To analyze the binding ability of the three anti-CHIK.E2 MAbs under detergent conditions, CHIK virus was incubated with 2% Triton X-100 and then coated on the ELISA plates. Only MAb 8A4 showed significant reactivity with CHIK virus under the denaturing conditions (data not shown), indicating that the MAb 8A4 is able to recognize CHIK E2 glycoprotein in the presence of non-ionic detergent.

Figure 4:
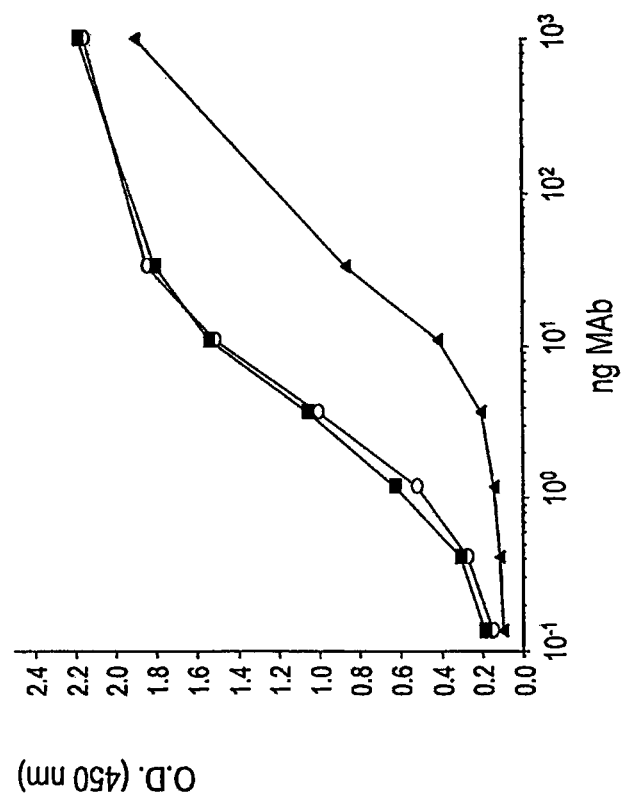
FIG. 4: Sensitivity of E2 detection using anti-CHIK.E2 MAbs. Sucrose-purified CHIK virus was used to coat the ELISA plates at $10^5$ FFU/well and increasing concentrations of MAbs 3C3 (▲) 3E4 (○), and 8A4 (■) were added. The reactivity of MAbs was tested by indirect ELISA as described in Methods.

In indirect ELISA, dose-curve responses showed that MAbs 8A4 and 3E4 bound better to CHIK virus than it did MAb 3C3 (FIG. 4). As estimated by this antigen detection test, the reactivity of MAb 3C3 was ten-fold lower compared to MAbs 8A4 and 3E4. To assess whether the pairs of anti-CHIK E2 MAbs can be useful for a sandwich assay, complementarity study was performed on recombinant soluble CHIK.sE2 protein by ProteOn biosensor analysis. MAbs 3C3 and 3E4 showed significant reactivity with CHIK.sE2 bound to MAb 8A4 and the best result was obtained when MAb 3E4 was used as detecting antibody (data not shown). Thus, the combination of anti-CHIK.E2 MAbs 8A4 (capture antibody) and 3E4 (detecting antibody) is suitable for the development of antigen-capture ELISA.

Figure 5:
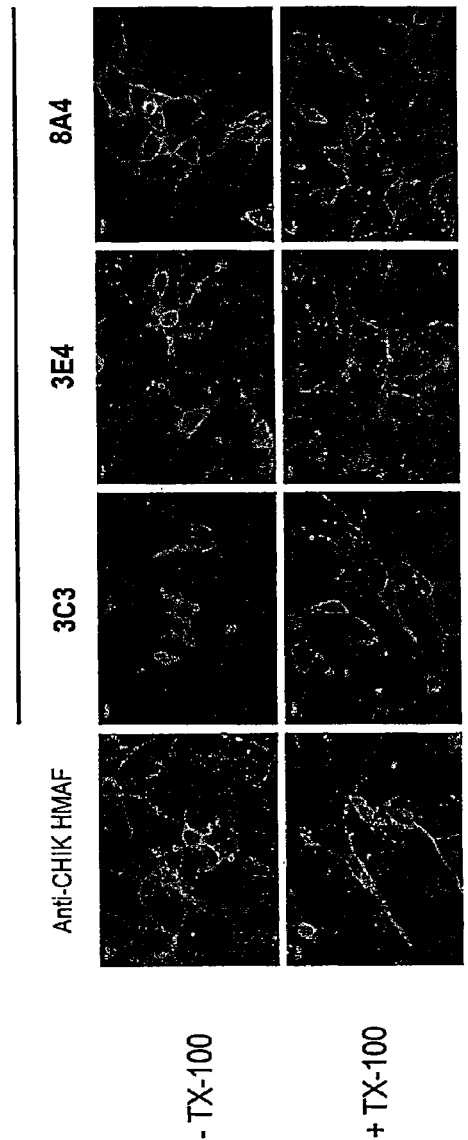
FIG. 5: Reactivity of anti-CHIK.E2 MAbs with endogenously synthesized E2 in infected cells. Vero cells were infected 24 h with CHIK.06-49 virus at 0.4 MOI. In (A), detection of E2 by IF assay using anti-CHIK.E2 MAbs. Fixed cells were permeabilized (+TX-100) or not permeabilized (−TX-100) and then immunostained with 2.5 µg·mL$^{-1}$ MAb 3C3, 3E4, or 8A4. Anti-CHIK HMAF (dilution 1:500) was used as a control. In (B), flow cytometry analysis of CHIK virus-infected cells using anti-CHIK.E2 MAbs. Fixed infected cells (continuous line) or mock-infected cells (dotted line) were permeabilized with saponin (black line) or not permeabilized (grey line) and then immunostained with 2.5 µg·mL$^{-1}$ MAb 3C3, 3E4, or 8A4. Anti-CHIK HMAF (dilution 1:500) was used as a positive control.

The binding ability of MAbs to CHIK E2 glycoprotein was further investigated by IF assay (FIG. 5A) and flow cytometry analysis (FIG. 5B). Anti-CHIK HMAF was used as a positive control. In IF assay, MAbs 3C3, 3E4, and 8A4 strongly reacted with endogenously synthesized E2 proteins in CHIK virus-infected Vero cells (FIG. 5A). As a negative control, anti-DEN E MAb 4E11 showed no reactivity (data not shown). All of three anti-CHIK.E2 MAbs recognized the CHIK E2 glycoprotein transported at the PM (FIG. 5A, −TX-100), suggesting that their epitopes are accessible on the outer face of E2. By flow cytometry analysis, MAbs 3C3 and 3E4 showed similar means of fluorescent intensity on CHIK virus-infected Vero cells permeabilized or not with saponin (FIG. 5B). Thus, both anti-CHIK.E2 MAbs are able to recognize similarly newly synthesized E2 molecules and PM-associated E2.

Flow cytometry analysis revealed that reactivity of anti-CHIK.E2 MAb 8A4 was distinct from MAbs 3C3 and 3E4. Indeed, MAb 8A4 showed a weaker reactivity with CHIK virus-infected cells in the presence of saponin (FIG. 5B). Because MAb 8A4 targets preferentially PM-associated E2, it is likely that its epitope is predominantly exposed on the external face of native-form of E2.

Immunoblot Reactivity of anti-CHIK.E2 MAbs

Figure 6:
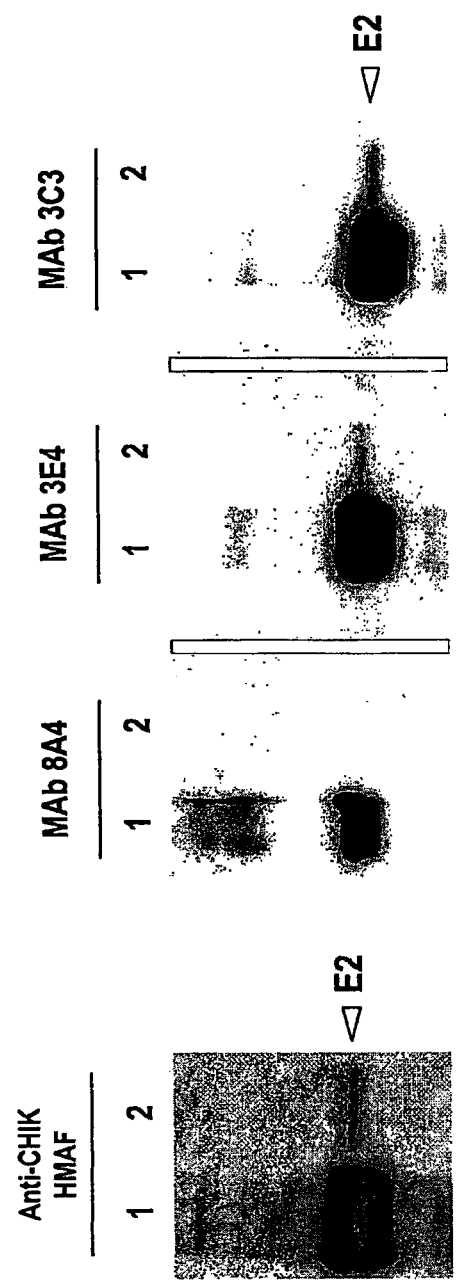
FIG. 6: Reactivity of anti-CHIK.E2 MAbs to reduced E2 proteins was determined by immunoblot analysis. Membranes blotted with 100 ng of purified CHIK.sE2 protein (lane 1) or $10^5$ FFU of sucrose-purified CHIK virus (lane 2) and were individually incubated with MAb 3C3, 3E4, or 8A4 as described in Methods. Anti-CHIK HMAF was used as a positive control.

Immunoblotting was performed with sucrose-purified CHIK virions and recombinant soluble CHIK.sE2 protein in order to determine whether anti-CHIK.E2 MAbs bound to linear epitopes (FIG. 6). As a positive control, anti-CHIK HMAF probed CHIK virus-associated E2 and CHIK.sE2. The inventors observed that MAbs 3C3 and 3E4 were able to react with E2 under the reducing conditions. To determine whether these MAbs recognize linear peptide epitopes, an array of immobilized overlapping 15-mer peptides covering the entire amino acid sequence of CHIK.sE2 was prepared by means of the SPOT technique. Linear synthetic peptides were incapable of forming epitopes for the two anti-CHIK.E2 MAbs (data not shown). These results suggest that MAbs 3C3 and 3E4 recognized partially linear epitopes.

Anti-CHIK.E2 MAb 8A4 failed to react with CHIK virus-associated E2 protein in immunoblot analysis (FIG. 6), suggesting that this MAb could recognize a conformational epitope. While MAb 8A4 has weaker reaction with CHIK.sE2 under the reducing conditions as compared to MAbs 3C3 and 3E4, it showed reactivity with two additional protein bands with estimated molecular weights of about 100 and 150 kDa (FIG. 6, MAb 8A4, lane 1). Such observation suggests that MAb 8A4 has the ability to detect dimeric and trimeric forms of soluble E2.

Cross-Reactivity of anti-CHIK.E2 MAbs with Old World alphaviruses

IF assays were performed on infected mosquito cells to assess whether the three anti-CHIK.E2 MAbs recognize SIN virus and related members of SF serocomplex isolated in Old World such as SF, Igbo-Ora, ONN, Babanki, Zingilamo, Middelburg, Ndumu, and Arv9/71 viruses. Table 2 summarizes the cross-reactivity of MAbs: anti-CHIK HMAF showed strong reactivity with CHIK S27 strain, Igbo-Ora IBH10964 strain, ONN Gulu (ONN-59) strain, Zingilamo AnB1245d strain, and SF IPD/A strain, moderate reactivity with SIN Ar399 strain, weak reactivity with Babanki ArY251 strain, and no cross-reactivity with Middelburg SAAr749 strain, Ndumu SAAr2204 strain, and Arv9/71 virus. The reactivity of anti-CHIK.E2 MAbs in the fluorescent antibody test was distinct from anti-CHIK HMAF. As shown by the results of IF assays, MAbs 3C3, 3E4, and 8A4 reacted with CHIK virus and to a lesser extent, Igbo-Ora virus (Table 2). In IF assay, MAb 8A4 showed similar reactivity with mosquito cells infected by CHIK virus or Igbo-Ora virus.

TABLE 2

Cross-reactivity of anti-CHIK E2 MAbs with alphaviruses using IF assay

| Virus[a] | anti-CHIK HMAF[b] | MAb 3C3[c] | MAb 3E4[d] | MAb 8A4[c] |
|---|---|---|---|---|
| CHIK | ++ | ++ | ++ | ++ |
| Igbo-Ora | ++ | + | + | ++ |
| ONN | ++ | − | − | − |
| Zingilamo | ++ | − | − | − |
| SF | + | − | − | − |
| SIN | + | − | − | − |
| Babanki | (+/−) | − | − | − |
| Middelburg | − | − | − | − |
| Ndumu | − | − | − | − |
| Arv9/71 | − | − | − | − |

[a]Fluorescent antibody test. Infected AP61 cells were fixed 24 h post-infection with PFA, permeabilized with Triton X-100 and immunostained as described in Methods. (++) strong, (+) moderate, and (+/−) low fluorescence signal. (−), no positive reaction. CHIK: Chikungunya, ONN: O'nyong-nyong, SF: Semliki Forest, SIN: Sindbis.
[b]mouse immune serum at 1:500 dilution
[c]the concentration of antibody was adjusted to 2.5 µg · mL$^{-1}$
[d]the concentration of antibody was adjusted to 3.0 µg · mL$^{-1}$ Alignment of amino acid sequences of the ectodomain and stem region of E2 (E2-1 to E2-364) for CHIK.06-49 virus, ONN-59 virus (Genbank accession n° M20303), and Igbo-Ora IBH 10964 strain (Genbank accession n° AF079457) is shown in FIG. 7. The two identified N-linked glycosylation sites at positions 263 and 345 are conserved in CHIK, ONN, and Igbo-Ora viruses. Genetic analysis on the first 365 residues of E2 identified as few as five amino acid differences (98.5% identity) between Igbo-Ora and ONN virus strains (FIG. 7). There are 45 amino acid differences (87.5% identity) between CHIK virus and the two other related members of SF antigenic complex. Comparative analysis of E2 sequences showed that ONN-59 differs from CHIK.06-49 and Igbo-Ora IBH 10964 viruses at positions E2-130, E2-164, and E2-288 (FIG. 7, open frames). Interestingly, the substitution Thr164Ala maps to strictly conserved region E2 160-177 in CHIK and Igbo-Ora viruses. This prolin-rich region might be exposed on the surface of the E2 spike in alphavirion (Mukhopadhyay et al., 2006).

Antigen-Capture ELISA Based on anti-CHIK E2 MAbs

Figure 8:
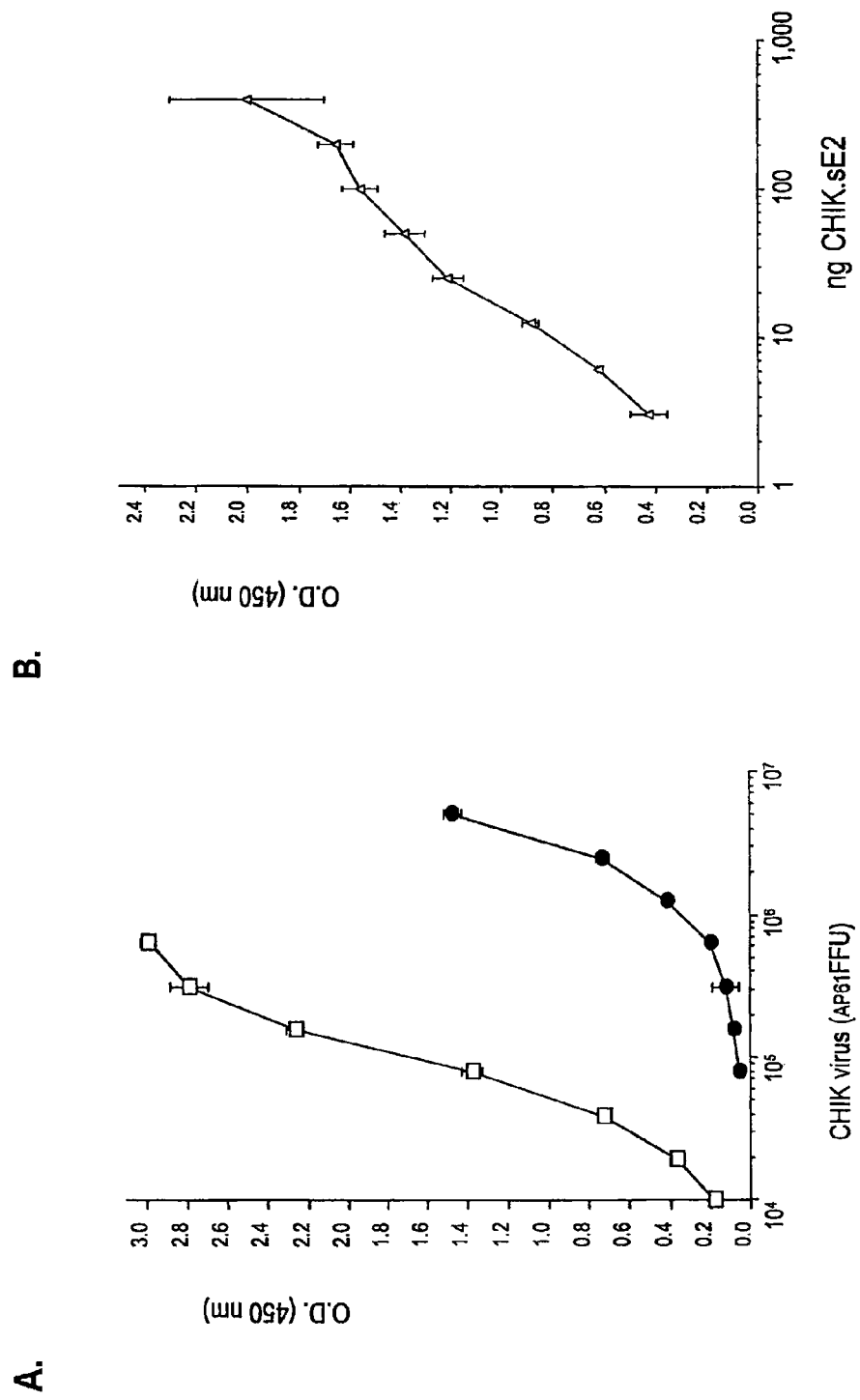
FIG. 8: Sensitivity of antigen-capture ELISA using anti-CHIK E2 MAbs. Quantitative analysis was performed using MAb 8A4 as capture antibody and MAb 3E4 as detecting antibody and virus culture supernatants (A) and recombinant soluble CHIK.sE2 glycoprotein as viral antigen (B). In (A), serially diluted CHIK.06-49 virus grown in mosquito AP61 cells (●) or human 293A cells (□). In (B) increasing concentrations of purified recombinant soluble CHIK.sE2 protein

As discussed above, anti-CHIK.E2 MAbs 8A4 and 3E4 are suitable for detection of CHIK virus in a sandwich ELISA. MAb 8A4 (2 µg·mL$^{-1}$) was used as capture antibody on the ELISA plates and peroxidase-conjugated MAb 3E4 (1 µg·mL$^{-1}$) as detecting antibody. To determine the sensitivity of antigen-capture ELISA, serial dilutions of CHIK.06-49 grown on mosquito AP61 or human 293A cells were used to determine standard curves (FIG. 8A). DPBST/1% milk was used to determine the baseline for antigen-capture at an optical density of 0.15 at 450 nm. Thus, the cut-off value for detection of CHIK viruses diluted in DPBST/1% milk was set to 0.45, which is equal to the mean+3 standard deviations (S.D.) of the OD450 for DPBST/1% milk. According the cut-off threshold, the detection limit of the ELISA was approximately $10^{6.0}$ AP61FFU of mosquito-cell-derived CHIK virus and $10^{4.3}$ FFU of human-cell-derived CHIK virus (FIG. 8A). Antigen-capture ELISA was also able to detect E2 in its soluble form (CHIK.sE2) and the minimal detectable mass was approximately 5 ng (FIG. 8B). The pair of anti-CHIK.E2 MAbs has higher level of reactivity with CHIK virus grown in 293A cells as compared to mosquito cells (FIG. 8A). This might be related to the release of individualized E2 glycoproteins in supernatants of human cells infected by cytopathic CHIK virus. These results show that MAbs 8A4 and 3E4 may be employed in combination to detect soluble CHIK E2 protein as well as virion-associated E2 protein in virus culture supernatant.

There are two distinct CHIK virus genotypes in Africa (reviewed by Powers and Logue, 2007). The first genotype comprised CHIK virus isolates from West Africa. The second genotype grouped CHIK virus isolates from East/Central/South Africa. To determine the specificity of the pair of anti-CHIK.E2 MAbs, antigen-capture ELISA tests were performed on a panel of clinical isolates of CHIK virus obtained from Central/East Africa (Central Africa Republic, 1978; Indian Ocean, 2005-06) and West Africa (Ivory Coast, 1999; Senegal, 1965-66 and 2005). All tested African strains of CHIK virus grown on mosquito cells were recognized (data not shown). Thus, the combination of MAbs 8A4 and 3E4 is able to recognize epitopes in E2 that are conserved across Western and Central/East African CHIK virus genotypes. To further define the specificity of the combination of anti-CHIK.E2 MAbs, antigen-capture ELISA was performed on related alphaviruses. The results were similar to those of indirect ELISA. Sandwiched MAbs 8A4 and 3E4 bound CHIK.06-49 strain and also to a lesser extent Igbo-Ora IBH 10964 strain, but did not cross-react with ONN-59 strain or other related members of SF antigenic complex isolated in Africa or Asia (data not shown). Together, these data demonstrate that the combination of anti-CHIK.E2 MAbs 8A4 and 3E4 is suitable in the design of sandwich assays for detection of CHIK virus, and to lesser extent Igbo-Ora virus.

Discussion

In this study, CHIK virus strain 06-49 isolated in La Réunion island in 2006 was used to generate a panel of MAbs against CHIK E2 glycoprotein in immunized mice. This report also describes a novel recombinant soluble CHIK E2 glycoprotein. The inventors expressed CHIK.sE2 which corresponds to CHIK.06-49 E2 ectodomain followed by its stem region in Drosophila S2 cells. In this expression system, CHIK.sE2 accumulated in the supernatants of induced stable S2 cells clones. Indirect ELISA and immunoblot assays showed that CHIK.sE2 was recognized by specific antibodies to CHIK virus. The inventors were able to develop purification procedures yielding highly purified CHIK.sE2 antigens.

The purified CHIK.sE2 protein from the S2 cell culture supernatant is suitable for easy detection of antibodies specific for CHIK virus in indirect ELISA and immunoblot analysis.

The inventors demonstrated that three anti-CHIK E2 MAbs (3C3, 3E4, and 8A4) have significant reactivity with CHIK virus-associated E2 glycoprotein in indirect ELISA. Because MAbs 3C3, 3E4 and 8A4 react with E2 in the context of an intact CHIK virion, their epitopes are probably located on the virus surface. However, all of three MAbs failed to neutralize CHIK virus infection of primate cells in vitro. Because the binding of anti-CHIK.E2 MAbs to whole virus did not inhibit the viral interaction with the host cells, it is likely that their epitopes did not map to major neutralizing domain of CHIK E2 glycoprotein.

The results of immunoblotting analysis showed that MAbs 3C3 and 3E4 have significant reactivity with CHIK virus-associated E2 and recombinant soluble CHIK E2 glycoprotein under the reducing conditions. Immunofluorescence studies showed that the two anti-CHIK E2 MAbs can successfully detect newly synthesized E2 as well as PM-associated E2 in infected primate cells. Based on their reactivity with CHIK antigens, it is presumed that epitopes recognized by MAbs 3C3 and 3E4 are least partly linear on the outer face of E2. Soluble CHIK.sE2 protein that is able to react with MAbs 3C3 and 3E4 could be useful as recombinant antigen for epitope mapping analysis. Evaluation of subfragments derived from CHIK.sE2 for competition binding studies is planned. Phage-displayed random peptides librairies are also likely applicable to identification of epitopes for anti-CHIK.E2 MAbs (Davis et al., 2000). In immunoblot analysis, MAb 8A4 failed to recognize CHIK virion-associated E2 and showed a weaker reactivity with CHIK.sE2 as compared to MAb 3C3 or 3E4 under the reducing conditions. The results of flow cytometry analysis showed that MAb 8A4 predominantly targets PM-associated E2 in CHIK virus-infected cells. Results of immunoblot analysis showed that MAb 8A4 could recognize homo-oligomeric forms of soluble E2 protein. Although atomic structure of CHIK E2 glycoprotein has yet to be determined, it is likely that epitope recognized by MAb 8A4 is conformational at the external face of native-form of E2.

The three anti-CHIK.E2 MAbs showed cross-reactivity with Igbo-Ora virus but not with ONN-59 strain as determined by IF assay. CHIK, ONN and Igbo-Ora viruses are serologically classified in the SF antigenic complex (reviewed by Strauss and Strauss, 1994). ONN virus was isolated from human samples in Uganda in 1959 (Haddow et al., 1960) and Igbo-Ora virus was isolated from humans in Nigeria in 1966 (Olaleye et al., 1988, 1990). It has been recently proposed that Igbo-Ora virus is a strain of ONN (Lanciotti et al., 1998; Powers et al., 2000).

The percent sequence identity values at E2 amino acid level indicated that Igbo-Ora strain BH10964 is more closely related to ONN-59 strain than is CHIK.06-49 strain isolated in La Réunion island in 2006 (FIG. 7). Given that E2 residue Thr164 is mutated to Ala in ONN virus strain Gulu isolated in 1959, the strictly conserved region E2 160-177 in CHIK and Igbo-Ora viruses (FIG. 7) might form part of the antigenic domain for these anti-CHIK.E2 MAbs. Indeed, the residues of this region might participate to the tip of the E2 spike of the E1-E2 heterodimers that cover the surface of alphavirion (Mukhopadhyay et al., 2006). Since ONN strain SG650 isolated in 1995 (ONN-95) possesses a threonin residue at position E2-164 (Lanciotti et al., 1998), further studies employing ONN-95 could potentially provide insight on the role of region E2 160-177 in the binding of anti-CHIK.E2 MAbs.

The presence of high titers of virus particles in virus culture supernatant and also the presence of E2 on the outer surface of virion as well as plasma membrane suggest that detection of CHIK virus infection should be based on virus antigens. Monoclonal antibody 8A4 is available for use in detecting a native CHIK virion and soluble form of the CHIK E2 glycoprotein. In antigen-capture ELISA, the pair of MAb 8A4 (capture antibody) and MAb 3E4 (detecting antibody) was able to detect at least $10^{4.5}$ FFU of CHIK virus grown in human cells. The detection limit of this test was about 5 ng of soluble E2 molecules. The pair of anti-CHIK E2 MAbs has the cross-reactivity for Central/East and West African strains of CHIK virus and no cross-reactivity with related members of SF complex with the notable exception of Igbo-Ora virus.

In conclusion, the inventors have generated and characterized three MAbs 3C3, 3E4, and 8A4 reactive to CHIK E2 glycoprotein. Such MAbs are helpful for studying the biology of CHIK virus and pathogenesis of Chikungunya fever (Borgherini et al., 2007; Ozden et al., 2007; Sourisseau et al., 2007). The three anti-CHIK E2 MAbs are useful in diagnostics of CHIK virus infection and the diagnostic methods may include the immunoblot and immunofluorescence assays (reviewed by Powers and Logue, 2007). The present data showed that MAbs 8A4 and 3E4 are also used in combination to recognize whole CHIK virus as well as soluble CHIK E2 glycoprotein in antigen detecting ELISA. Since the titer of infectious virus in blood and tissues is high enough to lead to early diagnosis of Chikungunya fever (Santhosh et al., 2007), it is clear that combination of anti-CHIK E2 MAbs 8A4 (capture antibody) and 3E4 (detecting antibody) is suitable for developing a specific and sensitive antigen detection system.

REFERENCES

Arankalle, V. A., Shrivastava, S., Cheman, S., Gunjikar, R. S., Walimbe, A. M., Jadhav, S. M., Sudeep, A. B. and Mishra, A. C., 2007. Genetic divergence of Chikungunya viruses in India (1963-2006) with special reference to the 2005-2006 explosive epidemic. J. Gen. Virol. 88, 1967-1976.

Blackburn, N. K., Besselaar, T. G. and Gibson, G., 1995. Antigenic relationship between chikungunya virus strains and o'nyong nyong virus using monoclonal antibodies. Res. Virol. 146, 69-73.

Borgehrini, G., Poubeau, P., Staikowski, F., Lory, M., Le Moullec, N., Becquart, J-P., Wengling, C., Michault, A., and Paganin, F. 2007. Outbreak of Chikungunya on Reunion island: Early diagnosis and laboratory features in 157 adult patients. J. Infect. Dis. 44, 1401-1407

Davis, J. M., Cai, Y-P., Weir, R. C., Rowley, M. J. (2000). Characterization of epitopes for virus-neutralizing monoclonal antibodies to Ross River virus E2 using phage-displayed random peptide libraries. Virology 275, 67-76

Edwards, C. J., Welch, S. R., Chamberlain, J., Hewson, R., Tolley, H., Cane, P. A., and Lloyd, G. 2007. Molecular diagnosis and analysis of Chikungunya virus. J. Clin. Virol. 39, 271-275

Epstein, P. R., 2007. Chikungunya Fever resurgence and global warming. Am. J. Trop. Med. Hyg. 76, 403-404.

Greiser-Wilke, I. M., Moennig, V., Kaaden, O. R. and Shope, R. E., 1991. Detection of alphaviruses in a genus-specific antigen capture enzyme immunoassay using monoclonal antibodies. J. Clin. Microbiol. 29, 131-137.

Haddow, A. J., Davies, C. W. and Walker, A. J., 1960. O'nyong nyong fever: an epidemic virus disease in East Africa. I. Introduction. Trans. R. Soc. Trop. Med. Hyg. 54, 517.

Johnston, R. E. and Peters, C. J., 1996. Alphaviruses associated primarily with fever and polyarthritis. In: Fields B N, Knipe D M, Howley P M, eds. Fields Virology. Philadelphia: Lippincott-Raven Publishers. 843-898.

Lanciotti, R. S., Ludwig, M. L., Rwaguma, E. B., Lutwama, J. J., Kram, T. M., Karabatsos, N., Cropp, B. C. and Miller, B. R., 1998. Emergence of epidemic O'nyong-nyong fever in Uganda after a 35-year absence: genetic characterization of the virus. Virology 252, 258-268.

Laurent, P., Le Roux, K., Grivard, P., Bertil, G., Naze, F., Picard, M., Staikowsky, F., Barau, G., Schuffenecker, I. and Michault, A., 2007. Development of a sensitive real-time reverse transcriptase PCR assay with an internal control to detect and quantify chikungunya virus. Clin. Chem. 53, 1408-1414.

Mukhopadhyay, S., Zhang, W., Gabler, S., Chipman, P. R., Strauss, E. G., Strauss, J. H., Baker, T. S., Kuhn, R. J. and Rossmann, M. G., 2006. Mapping the structure and function of the E1 and E2 glycoproteins in alphaviruses. Structure 14, 63-73.

Nakane, P. K. and Kawaoi, A., 1974. Peroxidase-labeled antibody. A new method of conjugation. J. Histochem. Cytochem. 22, 1084-1091.

Olaleye, O. D., Omilabu, S. A. and Fagbami, A. H., 1988. Igbo-Ora virus (an alphavirus isolated in Nigeria): a serological survey for haemagglutination inhibiting antibody in humans and domestic animals. Trans. R. Soc. Trop. Med. Hyg. 82, 905-906.

Olaleye, O. D., Omilabu, S. A. and Baba, S. S., 1990. Growth of Igbo-Ora virus in some tissue cultures. Acta Virol. 34, 367-371.

Ozden, S., Huerre, M., Riviere, J. P., Coffey, L. L., Afonso, P. V., Mouly, V., de Monredon, J., Roger, J. C., El Amrani, M., Yvin, J. L., Jaffar, M. C., Frenkiel, M. P., Sourisseau, M., Schwartz, O., Butler-Browne, G., Despres, P., Gessain, A. and Ceccaldi, P. E., 2007. Human muscle satellite cells as targets of chikungunya virus infection. PLoS ONE 2, e527.

Parida, M. M., Santhosh, S. R., Dash, P. K., Tripathi, N. K., Lakshmi, V., Mamidi, N., Shrivastva, A., Gupta, N., Saxena, P., Babu, J. P., Rao, P. V. and Morita, K., 2007. Rapid and real-time detection of Chikungunya virus by reverse transcription loop-mediated isothermal amplification assay. J. Clin. Microbiol. 45, 351-357.

Pialoux, G., Gauzere, B. A., Jaureguiberry, S. and Strobel, M., 2007. Chikungunya, an epidemic arbovirosis. Lancet Infect. Dis. 7, 319-327.

Plenetv, S. V., Zhang, W., Mukhopadhyay, S., Fisher, B. R., Hernandez, R., Brown, D. T., Baker, T. S., Rossman, M. G., and Kuhn, R. J. 2001. Location of carbohydrate sites on alphavirus glycoproteins show that E1 froms an icosahedral scaffold. Cell 105, 127-136

Powers, A. M., Brault, A. C., Tesh, R. B. and Weaver, S. C., 2000. Re-emergence of Chikungunya and O'nyong-nyong viruses: evidence for distinct geographical lineages and distant evolutionary relationships. J. Gen. Virol. 81, 471-479.

Rulli, N. E., Melton, J., Wimes, A., Ewartn G., and Mahalingam, S. 2007. The molecular and cellular aspects of arthritis due to alphavirus infection: lesson learned from Ross River virus. Ann. N. Acad. Sci. 1102, 96-108

Schuffenecker, I., Iteman, I., Michault, A., Murri, S., Frangeul, L., Vaney, M. C., Lavenir, R., Pardigon, N., Reynes, J. M., Pettinelli, F., Biscornet, L., Diancourt, L., Michel, S., Duquerroy, S., Guigon, G., Frenkiel, M. P., Brehin, A. C., Cubito, N., Despres, P., Kunst, F., Rey, F. A., Zeller, H. and Brisse, S., 2006. Genome microevolution of chikungunya viruses causing the Indian Ocean outbreak. PLoS Med. 3, e263.

Sourisseau, M., Schilte, C., Casartelli, N., Trouillet, C., Guivel-Benhassine, F., Rudnicka, D., Sol-Foulon, N., Roux, K. L., Prevost, M. C., Fsihi, H., Frenkiel, M. P., Blanchet, F., Afonso, P. V., Ceccaldi, P. E., Ozden, S., Gessain, A., Schuffenecker, I., Verhasselt, B., Zamborlini, A., Saib, A., Rey, F. A., Arenzana-Seisdedos, F., Despres, P., Michault, A., Albert, M. L. and Schwartz, O., 2007. Characterization of Reemerging Chikungunya Virus. PLoS Pathog. 3, e89.

Staikowsky, F., Le Roux, K., Schuffenecker, I., Laurent, P., Grivard, P., Develay, A. and Michault, A., 2007. Retrospective survey of Chikungunya disease in Reunion Island hospital staff. Epidemiol. Infect. 1-11.

Strauss, J. H. and Strauss, E. G., 1994. The alphaviruses: gene expression, replication, and evolution. Microbiol. Rev 58, 491-562.

---

The invention claimed is:

1. A monoclonal antibody specifically binding to an epitope located on the outer surface of a CHIK virus selected from the group deposited at the CNCM (Collection Nationale de Cultures de Microorganismes), 28 rue du Docteur Roux, 75724 Paris Cedex 15 on Sep. 6, 2007 under accession number I-3822 (3C3), I-3824 (3E4), and I-3823 (8A4).

2. A monoclonal antibody which specifically binds to a CHIK virus deposited at the CNCM (Collection Nationale de Cultures de Microorganismes), 28 rue du Docteur Roux, 75724 Paris Cedex 15, on Sep. 6, 2007 under accession number I-3823 (8A4).

3. A kit for detecting the presence or absence of a Chikungunya virus (CHIK) strain in a sample, comprising a monoclonal antibody selected from the group deposited at the CNCM (Collection Nationale de Cultures de Microorganismes), 28 rue du Docteur Roux, 75724 Paris Cedex 15, on Sep. 6, 2007 under accession number I-3822 (3C3), I-3824 (3E4), and I-3823 (8A4).

4. A kit for detecting the presence or absence of a Chikungunya virus (CHIK) E2 polypeptide in a sample, comprising a monoclonal antibody selected from the group deposited at the CNCM (Collection Nationale de Cultures de Microorganismes), 28 rue du Docteur Roux, 75724 Paris Cedex 15, on Sep. 6, 2007 under accession number I-3822 (3C3), I-3824 (3E4), and I-3823 (8A4).

5. A method for detecting the presence or absence of a Chikungunya virus (CHIK) strain in a sample, comprising the steps of:
   a) contacting the sample with an anti-CHIK monoclonal antibody or with a combination of anti-CHIK monoclonal antibodies to form an immune complex; and
   b) detecting the presence or absence of the immune complex formed in a);
   wherein said anti-CHIK antibody is selected from the group of monoclonal antibodies deposited at the CNCM (Collection Nationale de Cultures de Microorganismes), 28 rue du Docteur Roux, 75724 Paris Cedex 15, on Sep. 6, 2007 under accession number I-3822 (3C3) I-3824 (3E4), and I-3823 (8A4).

6. A method for detecting the presence or absence of envelope E2 polypeptide or functional derivative or its precursor E3E2 (p62) from Chikungunya (CHIK) E2 polypeptide in a sample, comprising the steps of:
   a) contacting the sample with an anti-CHIK E2 monoclonal antibody or with a combination of anti-CHIK monoclonal antibodies to form an immune complex; and
   b) detecting the presence or absence of the immune complex formed in a),
   wherein the monoclonal antibody specifically binds to an epitope located on the outer surface of a CHIK virus, with a binding affinity between the antibody and the epitope of at least $10^{-6}$ M, under competitive binding immunoassay conditions; and
   wherein said anti-CHIK antibody is selected from the group of monoclonal antibodies deposited at the CNCM (Collection Nationale de Cultures de Microorganismes) 28 rue du Docteur Roux, 75724 Paris Cedex 15, on Sep. 6, 2007 under accession number I-3822 (3C3), I-3824 (3E4), and I-3823 (8A4).

7. The method of claim 6, wherein the combination of anti-CHIK monoclonal antibodies consists of capture monoclonal antibody and a detecting monoclonal antibody.

8. The method of claim 7, wherein the capture monoclonal antibody consists of 8A4.

9. A method of screening of an infection by the CHIK virus comprising contacting a biological sample from a patient suspected of being infected with CHIK virus with a monoclonal antibody as claimed in claim 1, and detecting the presence or absence of a complex comprising the monoclonal antibody.

10. The method according to claim 9, wherein the infection by the CHIK virus is asymptomatic.

11. A method for detecting the presence or absence of envelope E2 polypeptide or functional derivative or its precursor E3E2 (p62) from Chikungunya (CHIK) E2 polypeptide in a sample, comprising the steps of:
   a) contacting the sample with an anti-CHIK E2 monoclonal antibody or with a combination of anti-CHIK monoclonal antibodies as claimed in claim 1 to form an immune complex; and
   b) detecting the presence or absence of the immune complex formed in a);
   wherein the combination of anti-CHIK monoclonal antibodies consists of capture monoclonal antibody and a detecting monoclonal antibody; and
   wherein the capture monoclonal antibody consists of 8A4 and the detecting monoclonal antibody consists of 3E4.

* * * * *

SEQUENCE LISTING

```
<160> NUMBER OF SEQ ID NOS: 6

<210> SEQ ID NO 1
<211> LENGTH: 364
<212> TYPE: PRT
<213> ORGANISM: Chikungunya virus

<400> SEQUENCE: 1

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60
```

```
Thr Lys Leu Arg Tyr Met Asp Asn His Met Pro Ala Asp Ala Glu Arg
 65                  70                  75                  80

Ala Gly Leu Phe Val Arg Thr Ser Ala Pro Cys Thr Ile Thr Gly Thr
                 85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
            115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
        275                 280                 285

Pro Asp His Pro Thr Leu Leu Ser Tyr Arg Asn Met Gly Glu Glu Pro
    290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro
        355                 360

<210> SEQ ID NO 2
<211> LENGTH: 364
<212> TYPE: PRT
<213> ORGANISM: Igbo Ora virus

<400> SEQUENCE: 2

Asn Ala Arg Glu Asn Phe Asn Val Tyr Lys Val Thr Arg Pro Tyr Leu
  1               5                  10                  15

Ala His Cys Pro Asp Cys Gly Glu Gly His Ser Cys His Ser Pro Ile
             20                  25                  30

Ala Leu Glu Arg Ile Arg Ser Glu Ala Thr Asp Gly Thr Leu Lys Ile
         35                  40                  45

Gln Val Ser Leu Gln Ile Gly Ile Lys Thr Ala Asp Ser His Asp Trp
     50                  55                  60

Thr Lys Leu Arg Tyr Met Asp Ser His Thr Pro Val Asp Ala Asp Arg
 65                  70                  75                  80
```

Ser Gly Leu Phe Val Arg Thr Ser Ala Pro Cys Thr Ile Thr Gly Thr
            85                  90                  95

Met Gly His Phe Ile Leu Ala Arg Cys Pro Lys Gly Glu Thr Leu Thr
            100                 105                 110

Val Gly Phe Val Asp Ser Arg Arg Ile Ser His Thr Cys Met His Pro
            115                 120                 125

Phe His His Glu Pro Pro Leu Ile Gly Arg Glu Lys Phe His Ser Arg
        130                 135                 140

Pro Gln His Gly Lys Glu Leu Pro Cys Ser Thr Tyr Val His Thr Thr
145                 150                 155                 160

Ala Ala Thr Thr Glu Glu Ile Glu Val His Met Pro Pro Asp Thr Pro
                165                 170                 175

Asp Tyr Thr Leu Met Thr Gln Gln Ala Gly Asn Val Lys Ile Thr Val
                180                 185                 190

Asp Gly Gln Thr Val Arg Tyr Lys Cys Lys Cys Asp Gly Ser Asn Glu
                195                 200                 205

Gly Leu Thr Thr Thr Asp Lys Val Ile Asn Asn Cys Lys Val Asp Gln
            210                 215                 220

Cys His Thr Ala Val Thr Asn His Lys Lys Trp Gln Tyr Asn Ser Pro
225                 230                 235                 240

Leu Thr Pro Arg Asn Ser Glu Gln Gly Asp Arg Lys Gly Lys Ile His
                245                 250                 255

Ile Pro Phe Pro Leu Val Asn Thr Thr Cys Arg Val Pro Lys Ala Arg
                260                 265                 270

Asn Pro Thr Val Thr Tyr Gly Lys Asn Arg Val Thr Leu Leu Leu Tyr
            275                 280                 285

Pro Asp His Pro Thr Leu Leu Ser Tyr Arg Ala Met Gly Arg Ile Pro
        290                 295                 300

Asp Tyr His Glu Glu Trp Ile Thr Ser Lys Lys Glu Ile Ser Ile Thr
305                 310                 315                 320

Val Pro Ala Glu Gly Leu Glu Val Thr Trp Gly Asn Asn Asp Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro
            355                 360

<210> SEQ ID NO 3
<211> LENGTH: 364
<212> TYPE: PRT
<213> ORGANISM: O'nyong-nyong virus

<400> SEQUENCE: 3

Asn Ala Arg Glu Asn Phe Asn Val Tyr Lys Val Thr Arg Pro Tyr Leu
1               5                   10                  15

Ala His Cys Pro Asp Cys Gly Glu Gly His Ser Cys His Ser Pro Ile
                20                  25                  30

Ala Leu Glu Arg Ile Arg Ser Glu Ala Thr Asp Gly Thr Leu Lys Ile
            35                  40                  45

Gln Val Ser Leu Gln Ile Gly Ile Lys Thr Asp Ser His Asp Trp
        50                  55                  60

Thr Lys Leu Arg Tyr Met Asp Ser His Thr Pro Val Asp Ala Asp Arg
65                  70                  75                  80

Ser Gly Leu Phe Val Arg Thr Ser Ala Pro Cys Thr Ile Thr Gly Thr
                85                  90                  95

-continued

```
Met Gly His Phe Ile Leu Ala Arg Cys Pro Lys Gly Glu Thr Leu Thr
            100                 105                 110

Val Gly Phe Val Asp Ser Arg Arg Ile Ser His Thr Cys Met His Pro
        115                 120                 125

Phe Arg His Glu Pro Pro Leu Ile Gly Arg Glu Lys Phe His Ser Arg
    130                 135                 140

Pro Gln His Gly Lys Glu Leu Pro Cys Ser Thr Tyr Val His Thr Thr
145                 150                 155                 160

Ala Ala Thr Ala Glu Glu Ile Glu Val His Met Pro Pro Asp Thr Pro
                165                 170                 175

Asp Tyr Thr Leu Met Thr Gln Gln Ala Gly Asn Val Lys Ile Thr Val
            180                 185                 190

Asp Gly Gln Thr Val Arg Tyr Lys Cys Lys Cys Asp Gly Ser Asn Glu
        195                 200                 205

Gly Leu Thr Thr Thr Asp Lys Val Ile Asn Asn Cys Lys Val Asp Gln
    210                 215                 220

Cys His Thr Ala Val Thr Asn His Lys Lys Trp Gln Tyr Asn Ser Pro
225                 230                 235                 240

Leu Thr Pro Arg Asn Ser Glu Gln Gly Asp Arg Lys Gly Lys Ile His
                245                 250                 255

Ile Pro Phe Pro Leu Val Asn Thr Thr Cys Arg Val Pro Lys Ala Arg
            260                 265                 270

Asn Pro Thr Val Thr Tyr Gly Lys Asn Arg Val Thr Leu Leu Leu His
        275                 280                 285

Pro Asp His Pro Thr Leu Leu Ser Tyr Arg Ala Met Gly Arg Ile Pro
    290                 295                 300

Asp Tyr His Glu Glu Trp Ile Thr Asn Lys Lys Glu Ile Ser Ile Thr
305                 310                 315                 320

Val Pro Ala Glu Gly Leu Glu Val Thr Trp Gly Asn Asn Asp Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro
        355                 360

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaaaagatc tgacaacttc aatgtctata aagccacaag acc                   43

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttttgcggc cgcgtcatag tggggtacag ctcataataa tacag                 45

<210> SEQ ID NO 6
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```